United States Patent [19]

Hori et al.

[11] Patent Number: 4,902,436

[45] Date of Patent: Feb. 20, 1990

[54] PROCESS FOR PRODUCING A MIXTURE OF SULFIDES OF ALKALINE EARTH METAL SALTS OF ALKYLHYDROXYBENZOIC ACID AND ALKYLPHENOL

[75] Inventors: Takashi Hori; Sanae Ueda, both of Saitama; Yoshihiro Kojima, Ibaraki; Hitoshi Kumagai, Saitama, all of Japan

[73] Assignee: Cosmo Oil Co., Ltd., Tokyo, Japan

[21] Appl. No.: 223,488

[22] Filed: Jul. 25, 1988

[30] Foreign Application Priority Data

Jul. 24, 1987 [JP] Japan ................................ 62-185057

[51] Int. Cl.$^4$ .......................................... C10M 159/22
[52] U.S. Cl. ..................................... 252/33.2; 252/39; 252/42.7
[58] Field of Search ....................... 252/33, 33.2, 42.7, 252/39; 568/716

[56] References Cited

U.S. PATENT DOCUMENTS 4,057,504 11/1977 Shiga et al. ............................ 252/33
4,518,807 5/1985 Hori et al. ............................. 568/716
4,710,308 12/1987 Stauffer ................................ 252/42.7
4,744,921 5/1988 Liston .................................. 252/33

FOREIGN PATENT DOCUMENTS 127396 8/1985 Japan .

Primary Examiner—Jacqueline V. Howard
Attorney, Agent, or Firm—Sughrue, Mion, Zinn, Macpeak & Seas

[57] ABSTRACT

A process for producing a mixture of sulfides of alkaline earth metal salts of an alkylhydroxybenzoic acid and an alkylphenol comprising the steps of: reacting a mixture of a phenol, a dihydric alcohol and an alkaline earth metal oxide and/or hydroxide (hereinafter referred to as an alkaline earth metal reagent) in an amount of no more than 0.99 gram equivalents per gram equivalent of said phenol; distilling off water and the dihydric alcohol until the amount of the dihydric alcohol becomes no more than 0.6 moles per mole of the alkaline earth metal reagent; reacting the resulting distillation residue with carbon dioxide; and reacting the resulting product with elemental sulfur in an amount of 0.1–4.0 moles per mole of the alkaline earth metal reagent.

31 Claims, No Drawings

PROCESS FOR PRODUCING A MIXTURE OF SULFIDES OF ALKALINE EARTH METAL SALTS OF ALKYLHYDROXYBENZOIC ACID AND ALKYLPHENOL

FIELD OF THE INVENTION

Hydroxybenzoic acids have been known as multifunctional materials and their use as additives to be incorporated in lubricating oils has been the subject of various studies for many years. Compounds that form a major class of such materials are (1) alkaline earth metal salts of alkylhydroxybenzoic acids. Some of these materials have already been developed and commercialized. Materials that constitute another interesting class are (2) sulfides of alkaline earth metal salts of alkylhydroxybenzoic acids.

The present invention relates to a novel sulfide in the second class (2) above and a process for producing the same. Stated more specifically, one aspect of the present invention is a process for producing a mixture containing a sulfide of an alkaline earth metal salt of an alkylhydroxybenzoic acid (an alkyl-substituted hydroxybenzoic acid). Another aspect of the present invention is a composition of the sulfide obtained by this process.

BACKGROUND OF THE INVENTION

The first attempt to introduce sulfur into an alkaline earth metal salt of an alkylhydroxybenzoic acid was made by Orland M. Reiff, as disclosed in U.S. Pat. No. 2,256,443. He first synthesized an alkali metal salt of an alkylsalicylic acid by the Kolbe-Schmitt process and introduced sulfur into said salt by reacting it with sulfur chloride in the presence of a butyl alcohol solvent and thereafter obtained a corresponding alkaline earth metal salt using an alcoholate of an alkaline earth metal. This method was unique in that it successfully reduced the generation of hydrogen chloride during the reaction.

At a later time, Jerome M. Cohen also introduced sulfur into an alkali metal salt of an alkylsalicylic acid that was synthesized by the Kolbe-Schmitt process as described in U.S. Pat. No. 3,595,791. His method consisted of subjecting said alkali metal salt to double decomposition with an alkaline earth metal halide to form a corresponding alkaline earth metal salt and reacting it with elemental sulfur in the presence of a glycol monoether and an alkaline earth metal oxide or hydroxide. The major feature of this method is that elemental sulfur, which is easy to handle, is used in place of a highly reactive sulfurizing reagent such as sulfur chloride.

However, the two methods described above have experienced the following problems, which make them unsuitable for use in commercial operations. First, they are complicated processes involving many steps. In the Reiff process, the product obtained by a sulfurization reaction has to be converted to a free acid form before the final product is attained. In the Cohen process, double decomposition with an alkaline earth metal halide is necessary after the Kolbe-Schmitt reaction. Secondly, both processes involve a step in which an alkali metal halide is formed as a by-product. Inclusion of such a strong electrolyte into a final product is not suitable in view of its quality. Reactions involving the combination of alkaline earth metal complexes of alkylphenols with carbon dioxide have been utilized for many years in the phenate industry which has competed with the salicylate industry [see Nishikawa and Ishibe, PETROTECH, 7, 338 (1984)].

However, as already described in U.S. Pat. No. 2,916,454, such combinations are unable to form a detectable amount of salicylic acids. In this process, alkylphenol sulfides were reacted with metal alcoholates and the resulting complexes were subjected to treatment with carbon dioxide at 125-200° C. and it was found that a carboxylation reaction did occur when the metal was an alkali metal, but not in the case where an alkaline earth metal was used.

One of the inventors of the present invention conducted studies on the process of phenate production comprising the steps of mixing and reacting an alkaline earth metal oxide or hydroxide, an alkylphenol, sulfur and a dihydric alcohol, thereafter distilling off water and excess dihydric alcohol, and subjecting the resulting sulfurized alkaline earth metal phenate to a treatment with carbon dioxide. In the course of these studies, he discovered the partial occurrence of a carboxylation reaction as disclosed in U.S. Pat. No. 4,123,371. What is interesting about this reaction is that it was carried out in the presence of a free alkylphenol although the presence of phenols had previously been considered to be deleterious to the formation of alkylsalicylic acids (see, for example, British Pat. No. 734,622, page 1, line 34 et seq).

The discovery of the above-described fact motivated the present inventors to develop sulfides of alkaline earth metal salts of alkylhydroxybenzoic acids. A thorough review of the factors associated with the conditions for this reaction (the study of which had led to the discovery described in U.S. Pat. No. 4,123,371 noted above), showed that problems still remained to be solved, not only in terms of the efficiency of carboxylation, but also in terms of the properties of the final product, including the oil solubility, stability and viscosity. However, the present inventors unexpectedly found that such aspects could be appreciably improved and a characteristic product could be attained by performing a sulfurization step after the treatment with carbon dioxide, rather than prior to it as had been the practice known in the art. The present invention has been accomplished on the basis of this finding.

SUMMARY OF THE INVENTION

It is one object of the present invention to provide a process for producing a novel mixture of sulfides of alkaline earth metal salts of an alkylhydroxybenzoic acid and an alkylphenol that has not been attainable in the prior art and which has a greater ability to neutralize acids.

Another object of the present invention is to provide an improved process for producing such a novel sulfide mixture by employing the minimum amount of starting materials and minimum processing steps.

These objects of the present invention are attained by a process for producing a mixture of sulfides of alkaline earth metal salts of an alkylhydroxybenzoic acid and an alkylphenol (the mixture is hereinafter referred to as a mixture of hydroxybenzoate/phenate sulfides) which comprises the steps of: reacting a mixture of a phenol, a dihydric alcohol and an alkaline earth metal oxide and-/or hydroxide (hereinafter referred to as an alkaline earth metal reagent) in an amount of no more than 0.99 gram equivalents per gram equivalent of said phenol; distilling off water and the dihydric alcohol until the amount of the dihydric alcohol becomes no more than 0.6 moles per mole of the alkaline earth metal reagent; reacting the resulting distillation residue with carbon dioxide; and reacting the resulting product with elemental sulfur in an amount of 0.1–4.0 moles per mole of the alkaline earth metal reagent.

DETAILED DESCRIPTION OF THE INVENTION

Phenols that can be used in the present invention include mono- and di-substituted phenols containing $C_{4-36}$, and preferably $C_{8-32}$, hydrocarbon side chains, such as alkyl, alkenyl and aralkyl groups. Specific examples include: phenols containing hydrocarbon groups such as butyl, amyl, octyl, nonyl, dodecyl, cetyl, ethylhexyl and triacontyl groups; and phenols having groups derived from petroleum hydrocarbons such as liquid paraffin, wax and olefinic polymers (e.g. polyethylene, polypropylene and polybutene). These phenols may be used either on their own or as admixtures. Generally preferred phenols are those which are capable of becoming liquid at a temperature of about 130° C., and preferably about 120° C. or higher. More specific examples of suitable phenols include: butylphenol, octylphenol, nonylhenol, dodecylphenol, cetylphenol, alkylphenols alkylated with polybutene, dinonylphenol, and didodecylphenol. Since phenols are monobasic acids, the term "one gram equivalent" as used with phenols refers to one mole.

Alkaline earth metal reagents are usually oxides or hydroxides of alkaline earth metals, such as calcium, barium, strontium, and magnesium. By using such alkaline earth metal reagents in amounts of not more than about 0.99 gram equivalents, preferably from about 0.01 to about 0.98 gram equivalents, per gram equivalent of the phenol, the desired mixture of hydroxybenzoate/phenate sulfides can be obtained. Even if the requirement that no more than about 0.99 gram equivalent ratio of the alkaline earth metal reagent to the phenol be used is satisfied, it is economically disadvantageous to use less than about 0.01 gram equivalent ratio of the alkaline earth metal reagent since not only is the yield of the product decreased, but also higher costs result from the necessity of recovering the unreacted phenol. On the other hand, if the gram equivalent ratio of the alkaline earth metal reagent to the phenol exceeds about 0.99, the conversion of the metal reagent is lowered and an undesirably large amount of insoluble matter will form, which increases the load of the removal operation. Furthermore, the product yield declines. One mole of an alkaline earth metal reagent is the same as 2 gram equivalents.

Useful dihydric alcohols are those which have relatively low boiling points and viscosities and which are highly reactive. For example, those having 2–6 carbon atoms, typically ethylene glycol and propylene glycol, are preferred. Dihydric alcohol is advantageously used in amounts of from about 0.15 to about 3.0 moles, preferably from about 0.5 to about 1.7 moles, per mole of the alkaline earth metal reagent. The dihydric alcohol assists in the conversion of the alkaline earth metal reagent to an oil-soluble substance by reaction between the phenol and the alkaline earth metal reagent. If the dihydric alcohol is used in too small of an amount, the conversion of reactants (in particular the alkaline earth metal reagent) to the final product decreases.

If desired, water may be added to the reaction system in the step of reacting the phenol with the alkaline earth metal reagent. Any type of water can be used, including distilled water, condensed water from boilers, industrial water and the water produced in the metal addition reaction. The water, if used, is added in an amount ranging from about 0 to about 2.0 moles, preferably from about 0.05 to about 1.5 moles, per mole of the alkaline earth metal reagent. The addition of water offers the advantage of permitting the metal addition reaction to proceed smoothly.

Elemental sulfur can be used in the present invention in a wide range of amounts. The sulfur is usually employed in an amount of from about 0.1 to about 4.0 moles, preferably from about 0.2 to 3.0 moles, per mole of the alkaline earth metal reagent used. If the amount of elemental sulfur used is outside range of from about 0.1 to 4.0 moles per mole of the alkaline earth metal reagent, a mixture of hydroxybenzoate/phenate sulfides having the desired properties cannot be obtained. One mole of elemental sulfur is equivalent to 32.1 g, or the atomic weight of sulfur.

In the present invention, diluents or solvents (hereinafter collectively referred to as "diluents") having suitable viscosities for facilitating the handling of reactants, reaction intermediates or the end product may be used at any stage of the process. For example, when excess unreacted phenol is to be recovered by distillation from the reaction product after completion of the sulfurization reaction, distillation residue or bottoms can be obtained in a desired liquid state by performing distillation in the presence of a diluent that boils at a high temperature and which has a suitable viscosity. Usually, part of the diluent used will distill off together with the unreacted phenol. Therefore, diluents that will not adversely affect the reaction are preferably used when the recovered phenol is to be cyclicaly subjected to the reaction. If desired, however, the reaction may be carried out in the presence of a diluent.

Preferred diluents are petroleum fractions, such as paraffinic, naphthenic, aromatic and mixed base oils having suitable viscosities and may be exemplified by lubricating oil fractions having boiling points of about 220°–550° C. and viscosities of about 0.5–40 cSt at 100° C. Other organic solvents can be used as diluents if they are hydrophobic and oleophilic and if they will not adversely affect the intended reaction or the product in end use.

The main process steps and operating conditions employed in the present invention for producing a mixture of hydroxybenzoate/phenate sulfides are described below in detail.

(A) Step of metal addition reaction

A mixture of a phenol, a dihydric alcohol, an alkaline earth metal reagent in an amount of no more than about 0.99 gram equivalents, preferably from about 0.98 to about 0.01 gram equivalents, per gram equivalent of the phenol, and optionally water in an amount of up to about 2.0 moles per mole of the alkaline earth metal reagent is subjected to reaction at a temperature of from about 60° to about 200° C., preferably from about 90° to about 190° C. The reaction is performed either at atmospheric pressure or at a superatmospheric pressure typically in the range of from about 0.01 to about 10 kg/cm$^2$G. If desired, this metal addition reaction may be performed in the presence of a diluent. Prior to the subsequent step of treatment with carbon dioxide, the water generated and added in the step consisting of the metal addition reaction is distilled off in an amount of at least about 95%, preferably at least about 99.9%, more preferably 100%, of the total quantity present. The dihydric alcohol is distilled off such that no more than about 0.6 moles, preferably no more than about 0.3 moles, per mole of the metal reagent used will remain in the reaction system. If large amounts of water and dihydric alcohol remain in the reaction system, the degree of carboxylation to be conducted in the subsequent step of treatment with carbon dioxide will decrease, to yield a smaller amount of hydroxybenzoate. The metal addition reaction is substantially completed within a time period that usually ranges from about 1 to about 9 hours.

(B) Step of treatment with carbon dioxide

This step is performed to produce a hydroxybenzoate component by carboxylating the product of the previous metal addition reaction. In this step, the product of the metal addition reaction is reacted with carbon dioxide at a temperature of from about 150° to about 240° C., preferably from about 160° to about 230° C., at either atmospheric, subatmospheric or superatmospheric pressure within the range of from about 0.05 to about 100 $kg/cm^2A$ (absolute), preferably from about 0.1 to about 50 $kg/cm^2A$. This treatment with carbon dioxide is substantially completed within a time period that usually ranges from about 1 to about 10 hours.

(C) Step of sulfurization

The sulfurization step is performed in order to improve the properties of the product of the previous step of treatment with carbon dioxide, such as the oil solubility, the viscosity characteristics and the storage stability. In this step, the product of treatment with carbon dioxide is reacted with elemental sulfur in an amount of from about 0.1 to about 4.0 moles, preferably from about 0.2 to about 3.0 moles, per mole of the alkaline earth metal reagent in an inert gas or carbon dioxide gas atmosphere either at atmospheric pressure or at superatmospheric pressure, preferably in the range of from about 0.5 to about 20 $kg/cm^2G$ and at a temperature in the range of from about 140° to about 230° C., preferably from about 150° to about 200° C. The reaction is substantially completed within a time period that usually ranges from about 1 to about 20 hours.

By the procedures described above, a mixture of hydroxybenzoate/phenate sulfides are obtained. Details of the structure of the reaction product obtained by the process of the present invention are not completely clear, but it would be a mixture of compounds in which phenate skeletons themselves, or a phenate skeleton and a hydroxybenzoate skeleton, or hydroxybenzoate skeletons themselves, are bonded by sulfur atoms, and unsulfurized phenate and hydroxybenzoate. Formation of the hydroxybenzoate component can be detected by the presence of a free organic acid which is obtained by neutralization using an acid (e.g. sulfuric acid) of the final product. Principally for economic reasons, part or most of the unreacted phenol is preferably recovered from the product of the sulfidizing reaction. If desired, the recovered phenol may be recycled for use as a starting material. Any dihydric alcohol remaining in the reaction system is recovered together with the unreacted phenol. If distillation of the unreacted phenol and residual dihydric alcohol is performed in the presence of a conventional diluent such as a high-boiling point mineral oil which was added to the product of the sulfurization reaction, the distillation residue can be obtained in a desired liquid state. Any insoluble matter present in the distillation residue can be removed by a suitable method such as filtration or centrifugal separation either prior to or after the recovery of the phenol.

The process of the present invention employs an alkaline earth metal reagent in place of an alkali metal reagent in the metal addition reaction and it does not employ a halide as a sulfurizing reagent. The process is fairly simple and the number of starting materials is reduced. Yet the process of the present invention enables the easy production of a mixture of sulfides of alkaline earth metal salts of an alkylhydroxybenzoic acid and an alkylphenol which has heretofore been unattainable without passing through a complicated process using an alkali metal compound and a sulfur halide.

As a further advantage, the yield of the product is improved with respect to the metal reagent used. The present inventors also found that a product having improved oil solubility could be obtained by the process of the present invention even when the alkyl group in the alkylphenol used as a starting material contained no more than about 9 carbon atoms. In contrast, according to the Reiff process described in U.S. Pat. No. 2,256,443, the use of an alkylphenol in which the alkyl group contains at least 20 carbon atoms was necessary to give an oil-soluble product.

It is also expected that the present invention would be capable of easily producing a complex consisting of an alkaline earth metal in an amount of one mole per mole of the alkylhydroxybenzoic acid formed by a carboxylation reaction. This complex has conventionaly been synthesized by a complicated method in which an alkylsalicylic acid or a normal salt thereof (i.e., a monosodium salt) obtained by the Kolbe-Schmitt process is converted to a corresponding disodium salt, which is then subjected to double decomposition with an alkaline earth metal halide, as disclosed in U.S. Pat. No. 3,704,315.

The present invention is described in greater detail below with reference to specific working examples and comparative examples. It should, however, be noted that these examples are given for illustrative purposes only and are by no means intended to limit the scope of the present invention.

EXAMPLE 1

A 5-L autoclave equipped with a stirrer, a condenser tube, a nitrogen gas introducing tube and a thermometer was charged with 2379 g (10.8 moles) of nonylphenol and 205 g (3.6 moles) of 98.4% pure calcium oxide, and the charged contents were stirred. To the resulting suspension, 345 g (5.4 moles) of ethylene glycol containing 2.8 wt % water was added at 155° C. and at an applied pressure of 6 $kg/cm^2$ in a nitrogen stream. After reaction at 160° C. for 3 hours, the pressure in the reaction system was slowly reduced while the added water, the water generated during the reaction, most of the added ethylene glycol and part of the added nonylphenol were distilled off, thereby producing liquid distillation residue of a mustard color in an amount of 2358 g. At the time when the reaction was completed, the distillation residue had a temperature of 180° C., while the temperature of the distillate was 160° C. at 11 mmHg.

After the distillation residue (2358 g) had cooled to 120° C. (22 mmHg), carbon dioxide was blown at a flow rate of 275 ml/min (6 $kg/cm^2$) for 0.6 hours until the pressure increased to 5.3 $kg/cm^2$. After the temperature was raised to 178° C., carbon dioxide was again blown till the pressure increased to 6 $kg/cm^2$. By holding the residue in that state for 4 hours, a dark grayish yellow red liquid reaction product was obtained in an amount of 2508 g. This reaction product had a calcium content of 5.76 wt %. Two grams of this reaction product was transferred into a separating funnel, dissolved in 60 ml of ether and hydrolyzed with 15 ml of 1 N sulfuric acid with stirring for 60 minutes. After thorough washing with water, the ether layer was separated and the ether was removed with a rotary evaporator to yield a brown liquid product in an amount of 1.88 g. This liquid product had an acid value of 64 mg KOH/g.

A protion (i.e., 418 g) of the product prepared by the treatment with carbon dioxide in the autoclave was transfered into another autoclave having a capacity of 1 L, which was charged with 23.1 g (0.72 moles) of sulfur in a $CO_2$ stream at atmospheric pressure and at 149° C. Thereafter, the temperature in the autoclave was raised to 178° C. and the pressure was elevated with $CO_2$ to 6 kg/cm². The mixture was stirred at 178° C. for 4 hours to obtain a very dark yellowish red liquid product in an amount of 436.4 g. This product had an acid value of 53 mg KOH/g (as measured by the method described above; the method of acid value measurement was the same in the following examples and comparative examples).

A 1-L three-necked pear-shaped flask was charged with 392.3 g of the product of sulfurization reaction and 165.6 g of a 150 neutral oil (i.e., a paraffinic lubricating oil having a viscosity of 5.38 cSt at 100° C.). Most of the nonylphenol and a small part of the lubricating oil fraction were distilled off to obtain a distillation residue in an amount of 330.9 g. The temperature of the final distillate was 190° C. (2 mmHg). The insoluble matter present in a very small amount in the distillation residue was removed by filtration so as to obtain a final product as a very dark yellowish red clear viscous liquid material in an amount of 328.7 g, which had the properties shown in Table 1.

EXAMPLE 2

A portion (i.e., 413.2 g) of the product of treatment with carbon dioxide as obtained in Example 1 was transferred into a 1-L autoclave, which was charged with 23.1 g (0.72 moles) of sulfur in a nitrogen stream at atmospheric pressure and at 140° C. Thereafter, the temperature was raised to 178° C. and reaction was performed for 8 hours to obtain the product of sulfurization reaction in an amount of 416.2 g. This product had an acid value of 50 mg KOH/g.

A 1-L three-necked pear-shaped flask was charged with 381.4 g of the sulfurized reaction product and 185.9 g of a 150 neutral oil. By following the same procedures as in Example 1, a final product having the properties shown in Table 1 was obtained in an amount of 372.5 g.

EXAMPLE 3

A portion (i.e., 418 g) of the product of treatment with carbon dioxide obtained in Example 1, was transferred into a 1-L autoclave, which was charged with 23.1 g (0.72 moles) of sulfur in a nitrogen stream at atmospheric pressure and at 136° C. Thereafter, the temperature was raised to 178° C. and reaction was performed for 4 hours to obtain the product of sulfurization reaction in an amount of 427.2 g. This product had an acid value of 50 mg KOH/g.

A portion (i.e., 370.5 g) of this reaction product and 146.1 g of a 150 neutral oil were charged into a 1-L three-necked pear-shaped flask and subsequently treated as in Example 1 to yield 323.4 g of a final product having the properties shown in Table 1.

COMPARATIVE EXAMPLE 1

A portion (i.e., 378.6 g) of the product of treatment with carbon dioxide as obtained in Example 1, and 185.9 g of a 150 neutral oil were charged into a 1-L three-necked pear-shaped flask and subsequently distilled as in Example 1, except that the sulfurization was not performed, to yield 360.1 g of a final product having the properties shown in Table 1.

The results of this comparative example show that an unsulfurized hydroxybenzoate having about 9 carbon atoms in a side-chain alkyl group was low in oil solubility and had a very high viscosity.

TABLE 1
Properties of Final Products

| Parameter | Example 1 | Example 2 | Example 3 | Comparative Example 1 |
|---|---|---|---|---|
| Viscosity (cSt at 100° C.) | 131.3 | 157.7 | 673.0 | 4450 |
| Base number (mg KOH/g) | 174 | 159 | 171 | 162 |
| Solubility*[1] | soluble | soluble | soluble | insoluble |
| Moisture stability*[2] (h) | ≧240 | 51 | 5 | — |
| Calcium content (wt %) | 6.20 | 5.67 | 6.12 | 5.8 |
| Sulfur content (wt %) | 3.32 | 2.89 | 3.43 | — |
| Acid value (mg KOH/g) | 46 | 37.5 | 44 | 46 |

Solubility*[1]Solubility as measured in Middle East paraffinic 50 engine oil after stirring at 60° C. for 5 minutes
Moisture stability*[2]Time of exposure to 98% rh and 28° C. before a film formed on the surface of an oil composition having a base number of 77 mg KOH/g and which was prepared from Middle East paraffinic 50 engine oil and the final product

EXAMPLE 4

A 5-L autoclave equipped with a stirrer, a condenser tube, a nitrogen gas introducing tube and a thermometer, was charged with 2316 g (10.5 moles) of nonylphenol and 201 g (3.5 moles) of 97.5% pure calcium oxide, and the charged contents were stirred. To the resulting suspension, 270.5 g (4.2 moles) of ethylene glycol containing 3.5 wt % water was added at 155° C. and at an applied pressure of 4 kg/cm² in a nitrogen stream. After reaction at 160° C. for 3 hours, the pressure in the reaction system was slowly reduced while the added water, the water generated during the reaction, most of the added ethylene glycol and part of the added nonylphenol were distilled off, thereby producing a liquid distillation residue of a mustard color in an amount of 2281 g. At the time when the reaction was completed, the distillation residue had a temperature of 178° C. while the temperature of the distillate was 154° C. at 15 mmHg.

After the distillation residue (2281 g) had cooled to 136° C. (28 mmHg), carbon dioxide was blown at a flow rate of 275 ml/min (6 kg/cm²) for 0.5 hours until the pressure increased to 5.6 kg/cm². After the temperature was raised to 220° C., carbon dioxide was blown again to a pressure of 6 kg/cm². By holding the residue in that state for 2 hours, a dark grayish yellow red liquid reaction product was obtained in an amount of 2374 g. To this reaction product, 1080 g of a 150 neutral oil was added. The resulting oily solution had an acid value of 46 mg KOH/g.

A portion (566 g) of the product prepared by the treatment with carbon dioxide in the autoclave was transferred into another autoclave (1 L capacity), which was charged with 7.3 g (0.23 moles) of sulfur in a $CO_2$ stream at atmospheric pressure and at 177° C. Thereafter, the contents were stirred at 178° C. for 4 hours at an applied $CO_2$ pressure of 6 kg/cm² to obtain the product of sulfurization reaction in an amount of 572.3 g. This product had an acid value of 38 mg KOH/g.

A 1-L three-necked pear-shaped flask was charged with 478.3 g of the product of sulfurization reaction and most of the nonylphenol and a small part of the lubricating oil fraction were distilled off to obtain a temperature of the final distillate was 193° C. (2 mmHg). The insoluble matter present in a very small amount in the distillation residue was removed by filtration, so as to obtain a final product as a very dark yellowish red clear viscous liquid material in an amount of 275.2 g which had the properties shown in Table 2.

EXAMPLE 5

An oily solution containing 480 g of the product of treatment with carbon dioxide as prepared in Example 4 was transferred into a 1-L autoclave, which was charged with 32.8 g (1.0 mole) of sulfur in a $CO_2$ stream at atmospheric pressure and at 172° C. Thereafter, the temperature was raised to 178° C. and the pressure was elevated to 6 kg/cm$^2$ by blown $CO_2$. By performing a reaction under these conditions for 4 hours, the product of sulfurization reaction was obtained in an amount of 506.2 g. This product had an acid value of 32 mg KOH/g.

A portion (i.e., 432.4 g) of the reaction product was charged into a 1-L three-necked pear-shaped flask and treated as in Example 4, to yield a final product in an amount of 265.3 g having the properties shown in Table 2.

EXAMPLE 6

An oily solution containing 480 g of the product of treatment with carbon dioxide as prepared in Example 4 was transferred into a 1-L autoclave, which was charged with 23.4 g (0.73 moles) of sulfur at 185° C. and at an applied $CO_2$ pressure of 6 kg/cm$^2$. Thereafter, the temperature was raised to 220° C. and reaction was performed for 4 hours to obtain the product of sulfurization reaction in an amount of 493.9 g. This product had an acid value of 19.5 mg KOH/g. A portion (i.e., 383.6 g) of this reaction product was charged into a 1-L three-necked pear-shaped flask and treated as in Example 4, to yield a final product in an amount of 231.7 g having the properties shown in Table 2.

COMPARATIVE EXAMPLE 2

An oily solution containing 442 g of the product of treatment with carbon dioxide as prepared in Example 4, was transferred into a 1-L autoclave, which was charged with 18.6 g (0.58 moles) of sulfur at 100° C. and at an applied $CO_2$ pressure of 6 kg/cm$^2$. Thereafter, the contents were stirred for 4 hours under these conditions to obtain the product of sulfurization reaction in an amount of 460 g. This product had an acid value of 42 mg KOH/g.

A portion (i.e., 417.3 g) of this reaction product was charged into a 1-L three-necked pear-shaped flask and treated as in Example 4 to yield a final product in an amount of 249.9 g having the properties shown in Table 2.

The results of this comparative example show that the properties of the final product, such as its oil solubility and viscosity, were not fully improved when the temperature for sulfurization reaction was low.

TABLE 2

| Parameter | Example 4 | Example 5 | Example 6 | Comparative Example 2 |
|---|---|---|---|---|
| Viscosity (cSt at 100° C.) | 148.1 | 156.8 | 191.1 | 885.3 |
| Base number (mg KOH/g) | 189 | 169 | 177 | 180 |
| Solubility*1 | soluble | soluble | soluble | insoluble |
| Moisture stability*2 (h) | 1 | ≧240 | ≧240 | — |
| Calcium content (wt %) | 6.75 | 6.05 | 6.32 | 6.54 |
| Sulfur content (wt %) | 1.20 | 3.60 | 3.93 | 3.24 |
| Acid value (mg KOH/g) | 47 | 30 | 26 | 33 |

Solubility*1 Solubility as measured in Middle East paraffinic 50 engine oil after stirring at 60° C. for 5 minutes
Moisture stability*2 Time of exposure to 98% rh and 28° C. before a film formed on the surface of an oil composition having a base number of 77 mg KOH/g and which was prepared from Middle East paraffinic 50 engine oil and the final product

EXAMPLE 7

A 1-L autoclave equipped with a stirrer, a condenser tube, a nitrogen gas introducing tube and a thermometer, was charged with 386.4 g of recovered nonylphenol (89.8% nonylphenol, 1.4% ethylene glycol and 8.8% mineral oil), 115.7 g of fresh nonylphenol and 40.3 g (0.7 moles) of 97.4% pure calcium oxide, and the charged contents were stirred. To the resulting suspension, 61.7 g (0.96 moles) of ethylene glycol containing 3.1 wt % of water was added at 155° C. and at an applied pressure of 4 kg/cm$^2$ in a nitrogen stream. After reaction at 160° C. for 3 hours, the pressure in the reaction system was slowly reduced while the added water, the water generated during the reaction, the ethylene glycol and part of the added nonylphenol were distilled off, thereby producing a liquid distillation residue of a mustard color in an amount of 534 g. At the time when the reaction was completed, the distillation residue had a temperature of 176° C. while the temperature of the distillate was 150° C. at 27 mmHg. Analysis of the distillate showed that the distillation residue had the ethylene glycol component left in an amount of 0.3 moles per mole of calcium.

After the distillation residue (534 g) had cooled to 132° C. (20 mmHg), carbon dioxide was blown at a flow rate of 50 ml/min (6 kg/cm$^2$) for 0.9 hours until the pressure increased to 5.8 kg/cm$^2$. After the temperature was raised to 178° C., carbon dioxide was blown again to a pressure of 6 kg/cm$^2$. By holding the residues in that state for 4 hours, a dark grayish yellow red liquid reaction product was obtained in an amount of 566.1 g. This reaction product had an acid value of 33 mg KOH/g.

Sulfur (28.4 g) was added to the reaction product (551 g) in the autoclave in a $CO_2$ stream at atmospheric pressure and at 177° C. Thereafter, the contents were stirred for 4 hours at an applied $CO_2$ pressure of 6 kg/cm$^2$ and at 178° C. so as to obtain the product of sulfurization reaction in an amount of 559.3 g. This reaction product had an acid value of 23 mg KOH/g.

A 1-L three-necked pear-shaped flask was charged with 306.4 g of the product of sulfurization reaction and 111.6 g of a 150 neutral oil. Most of the nonylphenol and a small part of the lubricating oil fraction were distilled off to obtain a distillation residue in an amount of 231.5 g. The temperature of the final distillate was 172° C. (3 mmHg). The insoluble matter present in a very small amount in the distillation residue was removed by filtration so as to obtain a final product in an amount of 219 g which had the properties shown in Table 3.

EXAMPLE 8

A reactor (inner capacity, 2 L) of the same type as used in Example 7 was charged with 881.2 g (4.0 moles) of nonylphenol and 57.0 g (1.0 mole) of 98.4% pure calcium oxide, and the charged contents were stirred. To the resulting suspension, 73.3 g (0.6 moles) of ethylene glycol containing 49.1 wt % water was added in a nitrogen stream at 125° C. and at an applied pressure of 2 kg/cm$^2$. After reaction at 130° C. for 3 hours, the pressure in the reaction system was slowly reduced while the added water, the water generated during the reaction, the ethylene glycol and part of the nonylphenol were distilled off, thereby producing a liquid distillation residue of a mustard color in an amount of 952 g. At the time when the reaction was completed, the distillation residue had a temperature of 150° C. while the temperature of the distillate was 25° C. at 32 mmHg. Analysis of the distillate showed that the distillation residue had the ethylene glycol component left in an amount of 0.52 moles per mole of calcium.

After the distillation residue (952 g) had cooled to 120° C. (35 mmHg), carbon dioxide was blown at a flow rate of 50 ml/min (6 kg/cm$^2$) for 0.5 hours until the pressure increased to 5.0 kg/cm$^2$. After the temperature was raised to 175° C., carbon dioxide was blown again to a pressure of 6 kg/cm$^2$. By holding the residues in that state for 4 hours, a dark grayish yellow red liquid reaction product was obtained in an amount of 992 g. This reaction product had an acid value of 20 mg KOH/g.

Sulfur (40.9 g) was added to the reaction product (971.9 g) in the autoclave in a CO$_2$ stream at atmospheric pressure and at 172° C. Thereafter, the contents were stirred for 4 hours at an applied CO$_2$ pressure of 6 kg/cm$^2$ and at 178° C. so as to obtain the product of sulfurization reaction in an amount of 1010 g. This reaction product had an acid value of 12 mg KOH/g.

A portion (i.e., 1007 g) of this reaction product and 237.4 g of a 150 neutral oil were charged into a 2-L three-necked pear-shaped flask and treated as in Example 7 to yield a final product in an amount of 460.8 g which had the properties shown in Table 3.

COMPARATIVE EXAMPLE 3

The product of treatment with carbon dioxide was obtained in an amount of 560 g by repeating the procedures of Example 7 except that the treatment with carbon dioxide was conducted at 140° C. The product obtained had a very low acid value (6 mg KO/g), indicating the low yield of the hydroxybenzoate component.

COMPARATIVE EXAMPLE 4

A reactor of the same type as used in Example 7 was charged with 528.7 g (2.4 moles) of nonylphenol, 34.2 g (0.6 moles) of 98.4% pure calcium oxide and 13.5 g (0.42 moles) of sulfur, and the charged contents were stirred. To the resulting suspension, 46.3 g (0.72 moles) of ethylene glycol containing 3.5 wt % water was added in a nitrogen stream at 155° C. and at an applied pressure of 6 kg/cm$^2$. After reaction at 160° C. for 3 hours, the pressure in the reaction system was slowly reduced while the added water, the water generated during the reaction, most of the added ethylene glycol and part of the added nonylphenol were distilled off, thereby producing a very dark yellow liquid distillation residue in an amount of 541.5 g. At the time when the reaction was completed, the distillation residue had a temperature of 173° C. while the temperature of the distillate was 162° C. at 15 mmHg.

After the distillation residue (536 g) had cooled to 130° C. (35 mmHg), carbon dioxide was blown at a flow rate of 50 ml/min (6 kg/cm$^2$) for 0.6 hours until the pressure increased to 6 kg/cm$^2$. After the temperature was raised to 178° C., the residue was held at 6 kg/cm$^2$ for 4 hours, obtaining a very dark yellow liquid reaction product in an amount of 554 g. This liquid material had a acid value of 34 mg KOH/g.

A portion (i.e., 443.2 g) of this reaction product and 157 g of a 150 neutral oil were charged into a 1-liter three-necked pear-shaped flask and treated as in Example 7, yielding 256.1 g of a final product having the properties shown in Table 3.

The results of this comparative example show that when a sulfurization reaction was performed prior to treatment with carbon dioxide as in the conventional process for phenate sulfide production, an attempt to produce an increased amount of hydroxybenzoate component by carboxylation resulted in a final product that was unsatisfactory in such properties as viscosity, oil solubility, and moisture stability.

TABLE 3

Properties of Final Products

| Parameter | Example 7 | Example 8 | Comparative Example 4 |
|---|---|---|---|
| Viscosity (cSt at 100° C.) | 71.9 | 138.7 | 614.2 |
| Base number (mg KOH/g) | 171 | 231 | 182 |
| Solubility*[1] | soluble | soluble | insoluble |
| Moisture stability*[2] (h) | ≧240 | ≧240 | — |
| Calcium content (wt %) | 6.09 | 8.22 | 6.33 |
| Sulfur content (wt %) | 3.16 | 4.10 | 2.18 |
| Acid value (mg KOH/g) | 29 | 23 | 35 |

Solubility*[1] Solubility as measured in Middle East paraffinic 50 engine oil after stirring at 60° C. for 5 minutes
Moisture stability*[2] Time of exposure to 98% rh and 28° C. before a film formed on the surface of an oil composition having a base number of 77 mg KOH/g and which was prepared from Middle East paraffinic 50 engine oil and the final product

EXAMPLE 9

A final product having the properties shown in Table 4 was obtained in an amount of 263.6 g by repeating the procedures of Example 1 except that nonylphenol was replaced by 2.1 moles of dodecylphenol, calcium oxide by 0.7 moles of calcium hydroxide, and that the amount of ethylene glycol containing 2.8 wt % water was changed to 67.1 g (1.05 moles). The two reaction intermediates, i.e., the product of treatment with carbon dioxide and the product of sulfurization reaction, had acid values of 49 mg KOH/g and 36 mg KOH/g, respectively.

EXAMPLE 10

A final product having the properties shown in Table 4 was obtained in an amount of 123.4 g by repeating the procedures of Example 1 except that nonylphenol was replaced by 0.33 moles of a long-chain alkylphenol having an average molecular weight of 585 (hydroxyl value, 96), that the amount of ethylene glycol was changed to 0.29 moles, that no water was added, and that the amount of calcium oxide charged was changed to 0.14 moles. The two reaction intermediates, i.e., the product of treatment with carbon dioxide and the product of sulfurization reaction, had acid values of 27 mg KOH/g and 20 mg KOH/g, respectively.

EXAMPLE 11

A final product having the properties shown in Table 4 was obtained in an amount of 465.9 g by repeating the procedures of Example 1 except that the amount of nonylphenol was changed to 2.05 moles, that 308.6 g of 150 neutral oil was added before the metal addition reaction, that the amounts of calcium oxide charged and ethylene glycol containing 2.8 wt % water were changed to 1 mole and 96 g (1.5 moles), respectively.

EXAMPLE 12

A final product having the properties shown in Table 4 was obtained in an amount of 473 g by repeating the procedures of Example 1 except that the amount of nonylphenol, calcium oxide and ethylene glycol containing 2.8 wt % water were changed to 10 moles, 1 mole and 96 g, respectively.

TABLE 4
Properties of Final Products

| Parameter | Example 9 | Example 10 | Example 11 | Example 12 |
|---|---|---|---|---|
| Viscosity (cSt at 100° C.) | 215.9 | 192.4 | 143.1 | 137.5 |
| Base number (mg KOH/g) | 170 | 81 | 180 | 163 |
| Solubility*1 | soluble | soluble | soluble | soluble |
| Moisture stability*2 (h) | 240 | ≧240 | 72 | ≧240 |
| Calcium content (wt %) | 6.06 | 2.89 | 6.43 | 5.80 |
| Sulfur content (wt %) | 3.02 | 1.43 | 3.40 | 3.10 |
| Acid value (mg KOH/g) | 33 | 16 | 48 | 42 |

Solubility*1 Solubility as measured in Middle East paraffinic 50 engine oil after stirring at 60° C. for 5 minutes
Moisture stability*2 Time of exposure to 98% rh and 28° C. before a film formed on the surface of an oil composition having a base number of 77 mg KOH/g and which was prepared from Middle East paraffinic 50 engine oil and the final product In Example 1, calcium oxide was used in an amount of 0.67 gram equivalents per gram equivalent of nonylphenol; ethylene glycol, water and sulfur were used in amounts of 1.5 moles, 0.14 moles and 1.2 moles per mole of calcium oxide, respectively; the step of metal addition reaction was performed at 160° C.; the step of treatment with carbon dioxide was performed at 178° C.; and the sulfurization step was performed in a $CO_2$ atmosphere at 178° C. In Examples 2 and 3, the sulfurization step was performed in a nitrogen atmosphere. Examples 4 differed from Example 1 in that the treatment with carbon dioxide was performed at a higher temperature and sulfur was used in a smaller amount. In Example 5, sulfur was used in larger amount. In Example 6, the sulfurization reaction was performed at a higher temperature. In Example 7, a comparatively large amount of residual ethylene glycol was present after the distillation step following the metal addition reaction. In Example 8, ethylene glycol was used in a smaller amount, water was added in a larger amount, and a comparatively large amount of residual ethylene glycol was present after the distillation step following the metal addition reaction. In Example 9, dodecylphenol was used as a starting phenol and calcium hydroxide was used as an alkaline earth metal reagent. In Example 10, a long-chain alkylphenol was used as a starting phenol, an increased proportion of ethylene glycol was used, and no water was added. In Example 11, the ratio of the amount of alkaline earth metal reagent used to that of the phenol was increased. In Example 12, this ratio was decreased. In all of these examples of the present invention, mixtures of hydroxybenzoate/phenate sulfides having a high capability for acid neutralization were produced in high yields and easily at that.

While the invention has been described in detail and with reference to specific embodiments thereof, it will be apparent to one skilled in the art that various changes and modifications can be made therein without departing from the spirit and scope thereof.

What is claimed is:

1. A process for producing a mixture of sulfides of alkaline earth metal salts of an alkylhydroxybenzoic acid and an alkylphenol, said process comprising the steps of: reacting a mixture of a phenol, a dihydric alcohol and an alkaline earth metal oxide and/or hydroxide (hereinafter referred to as an alkaline earth metal reagent) in an amount of no more than 0.99 gram equivalents per gram equivalent of said phenol; distilling off water and the dihydric alcohol until the amount of the dihydric alcohol becomes no more than 0.6 moles per mole of the alkaline earth metal reagent; reacting the resulting distillation residue with carbon dioxide; and reacting the resulting product with elemental sulfur in an amount of 0.1–4.0 moles per mole of the alkaline earth metal reagent to conduct sulfurization.

2. A process according to claim 1, wherein the metal addition reaction is performed with water being added to the reaction system.

3. A process according to claim 1, wherein the metal addition reaction is performed in the presence of a diluent.

4. A process according to claim 3, wherein the diluent is a petroleum fraction.

5. A process according to claim 4, wherein said diluent is a paraffinic, naphthenic, aromatic or mixed base oil.

6. A process according to claim 1, wherein the metal addition reaction is performed at a temperature of 60–200° C.

7. A process according to claim 1, wherein the metal addition reaction is performed at a temperature of 90°–190° C.

8. A process according to claim 2, wherein the product of the metal addition reaction is distilled with at least 95% of the water added in the step of said metal addition reaction and the water generated during that reaction being distilled off.

9. A process according to claim 2, wherein the product of the metal addition reaction is distilled with at least 99.9% of the water added and generated during the metal addition reaction being distilled off.

10. A process according to claim 2, wherein the product of the metal addition reaction is distilled with substantially all of the water added and generated during the metal addition reaction being distilled off.

11. A process according to claim 1, wherein the product of the metal addition reaction is distilled with the dihydroric alcohol being distilled off until its amount becomes no more than 0.3 moles per mole of the alkaline earth metal reagent.

12. A process according to claim 1, wherein the product of the metal addition reaction is distilled with substantially all of the dihydric alcohol being distilled off.

13. A process according to claim 1, wherein the product of the metal addition reaction is distilled with substantially all of the water present being distilled off, and with substantially all of the dihydric alcohol being also distilled off.

14. A process according to claim 1, wherein the treatment with carbon dioxide is performed at a temperature of 150°–240° C.

15. A process according to claim 1, wherein the treatment with carbon dioxide is performed at a temperature of 160°–230° C.

16. A process according to claim 1, wherein the sulfurization step is performed at a temperature of 140°–230° C.

17. A process according to claim 1, wherein the sulfurization step is performed at a temperature of 150°–200° C.

18. A process according to claim 1, wherein a diluent is added to the product of sulfurization reaction and the mixture is distilled so as to distill off the unreacted phenol.

19. A process according to claim 18, wherein the diluent is a petroleum fraction.

20. A process according to claim 1, wherein any insoluble matter present is removed from the product of sulfurization reaction.

21. A process according to claim 1, wherein the phenol contains a hydrocarbon side chain having 4–36 carbon atoms.

22. A process according to claim 21, wherein said phenol is butylphenol, octylphenol, nonylphenol, dodecylphenol, cetylphenol, alkylphenols alkylated with polybutene, wax, or polypropylene, dinonylphenol, or didodecylphenol.

23. A process according to claim 1, wherein the phenol becomes liquid at a temperature of 120° C. or higher.

24. A process according to claim 1, wherein the alkaline earth metal reagent is an oxide or a hydroxide of calcium, barium, strontium or magnesium.

25. A process according to claim 1, wherein the alkaline earth metal reagent is used in an amount of 0.01–0.98 gram equivalents per gram equivalent of the phenol.

26. A process according to claim 2, wherein water is added in an amount of 0–2.0 moles per mole of the alkaline earth metal reagent.

27. A process according to claim 1, wherein the dihydric alcohol contains 2–6 carbon atoms.

28. A process according to claim 1, wherein the dihydric alcohol is ethylene glycol or propylene glycol.

29. A process according to claim 1, wherein the dihydric alcohol is used in an amount of 0.15–3.0 moles per mole of the alkaline earth metal reagent.

30. A process according to claim 1, wherein the dihydric alcohol is used in an amount of 0.5–1.7 moles per mole of the alkaline earth metal reagent.

31. A process according to claim 1, wherein sulfur is used in an amount of 0.2–3.0 moles per mole of the alkaline earth metal reagent.

* * * * *